United States Patent
An et al.

(10) Patent No.: US 9,400,263 B2
(45) Date of Patent: Jul. 26, 2016

(54) ROBOT FOR INSPECTING PIPELINES

(71) Applicant: Research & Business Foundation Sungkyunkwan University, Suwon-si (KR)

(72) Inventors: Jae Kyu An, Seoul (KR); Sang Chul Han, Seoul (KR); Hyungpil Moon, Seongnam-si (KR)

(73) Assignee: Research & Business Foundation SUNGKYUNKWAN UNIVERSITY, Suwon-si (KR)

( * ) Notice: Subject to any disclaimer, the term of this patent is extended or adjusted under 35 U.S.C. 154(b) by 227 days.

(21) Appl. No.: 14/093,129

(22) Filed: Nov. 29, 2013

(65) Prior Publication Data

US 2014/0156067 A1 Jun. 5, 2014

(30) Foreign Application Priority Data

Nov. 30, 2012 (KR) ........................ 10-2012-0137474

(51) Int. Cl.
*G01M 3/00* (2006.01)
*G01M 3/18* (2006.01)
*G01N 29/265* (2006.01)
*G01N 29/22* (2006.01)
*G01N 29/24* (2006.01)
*G01M 5/00* (2006.01)

(52) U.S. Cl.
CPC ........... *G01N 29/265* (2013.01); *G01M 5/0025* (2013.01); *G01M 5/0033* (2013.01); *G01M 5/0075* (2013.01); *G01N 29/225* (2013.01); *G01N 29/2412* (2013.01); *G01N 2291/2636* (2013.01)

(58) Field of Classification Search
CPC .............. G01N 29/225; G01N 29/265; G01N 29/2412; G01N 2291/2634; G01N 2291/0234; G01N 2291/0232; G01M 5/0025; G01M 5/0033
USPC ........ 73/622, 637, 865.8, 619; 901/44, 46, 12
See application file for complete search history.

(56) References Cited

FOREIGN PATENT DOCUMENTS

JP          5-139292 A       6/1993
KR    10-2012-0058872 A     6/2012

OTHER PUBLICATIONS

Korean Office Action issued Nov. 27, 2013 in counterpart Korean Patent Application No. 10-2012-0137474 ( 4 pages, in Korean).
Sang Chul Han et al., "Developmeny of Pipe Climbing Robot Module" Department of Mechanical Engineering, Sungkyunkwan University pp. 31-32 (Apr. 2012).

*Primary Examiner* — Peter Macchiarolo
*Assistant Examiner* — Anthony W Megna Fuentes
(74) *Attorney, Agent, or Firm* — NSIP Law

(57) ABSTRACT

Provided herein is a robot for inspecting pipelines as it moves along an outer surface of a pipeline, the robot comprising: a plurality of body parts detachably provided along a longitudinal direction of the pipeline; a connector configured to connect adjacent body parts, and to distance one of the connected body parts away from the pipeline so that the plurality of body parts may cross an obstacle; and a controller configured to control the connector to lift one of the body parts to cross an obstacle, with another body part secured to the pipeline.

10 Claims, 18 Drawing Sheets

ROBOT FOR INSPECTING PIPELINES

CROSS-REFERENCE TO RELATED APPLICATIONS

This application claims the benefit of priority under 35 U.S.C. §119(a) of Korean Patent Applications No. 10-2012-0137474, filed on Nov. 30, 2012, in the Korean Intellectual Property Office, the entire disclosure of which is incorporated herein by reference for all purposes.

BACKGROUND

1. Field

The following description relates to a robot for inspecting pipelines, for example, to a robot for inspecting pipelines, the robot capable of performing up-and-down motions, motions of rotating in place, and motions of crossing obstacles outside the pipelines.

2. Description of Related Art

Pipeline facilities are one of various infrastructure, and are distributed nationwide just like blood vessels in a human body, and are established as an origin of supply of various energy resources. These pipelines are being corroded as time goes by and deteriorating due to external environments, causing small and large pipeline accidents every year, and thus regular inspection and replacement of pipelines are necessary.

However, due to lack of manpower and technology, systematic and regular inspections are not being made in reality.

Especially, in the case of pipelines used in nuclear power plants, there is risk due to radiation leakage, but inspections are being made by men taking the risk of being exposed to radiation for the sake of conducting strict inspections.

If inspections could be conducted by robots, it would be able to inspect the condition of nuclear power plants without taking the risk of being exposed to radiation, and thus there has been need for ways to inspect pipelines using robots.

However, developing robots for inspecting pipelines so far concentrated on embodying motions of moving along curved ducts, and there has been no robot capable of performing motions, rotating motions and crossing of obstacles motions outside the pipelines, and thus robots could not be applied to the related field, which has been a problem.

SUMMARY

Therefore, the purpose of the present disclosure is to resolve the aforementioned problems of prior art, that is, to provide a robot for inspecting pipelines capable of moving along or rotating pipelines.

In a general aspect, there is provided a robot for inspecting pipelines as it moves along an outer surface of a pipeline, the robot comprising: a plurality of body parts detachably provided along a longitudinal direction of the pipeline; a connector configured to connect adjacent body parts, and to distance one of the connected body parts away from the pipeline so that the plurality of body parts may cross an obstacle; and a controller configured to control the connector to lift one of the body parts to cross the obstacle, with another body part secured to the pipeline.

In the general aspect of the robot, it is desirable that each of the plurality of body parts comprise a body; and a plurality of robot arms attached to the body and encircling at both sides of the pipeline.

In the general aspect of the robot, it is desirable that each of the plurality of robot arms perform a motion of approaching the pipeline or distancing away from the pipeline.

In the general aspect of the robot, it is desirable that each robot arm comprise a first robot arm configured to contact the pipeline and guide each body part to perform a straight line motion along a longitudinal direction of the pipeline, and a second robot arm configured to contact the pipeline and guide each body part to perform a rotating motion around a circumference direction of the pipeline.

In the general aspect of the robot, it is desirable that the first robot arm comprise a first robot arm member connected to the body part; and a first motion part provided between the first robot arm member and the pipeline, and rotates along a longitudinal direction of the pipeline.

In the general aspect of the robot, it is desirable that each first robot arm consists of a pair of robot arms, and comprises a first main robot arm configured to receive power from outside and move the body part, and a first auxiliary robot arm configured to assist the first main robot arm to guide a movement direction of the body part.

In the general aspect of the robot, it is desirable that the second robot arm comprises a second robot arm member connected to the body part; and a second motion part provided between the second robot arm member and the pipeline, and configured to rotate around a circumference direction of the pipeline.

In the general aspect of the robot, it is desirable that there is further provided a sensor provided in the body part, and configured to contact the pipeline to inspect the pipeline, wherein the sensor is interlocked with the first robot arm such that when the first robot arm distance away from the pipeline, the sensor approaches the pipeline.

In the general aspect of the robot, it is desirable that the sensor is an electromagnetic acoustic transducer (EMAT) configured to perform non-destructive test (NDT).

In the general aspect of the robot, it is desirable that the connector comprises a four bar link configured to connect the adjacent body parts, and to restrict the movement of the body parts, and lifts a first link or second link by an interlocked motion of the links to lift the body part connected to the first link or second link.

In the general aspect of the robot, it is desirable that the connector further comprises a gear part provided in the first link or second link, and configured to decelerate power from outside through the interlocked motion to increase an output torque.

In the general aspect of the robot, it is desirable that the gear part comprises a plurality of gears engaging adjacent gears, the gears arranged such that the farther away from the gear where power is applied, the greater the number or size of the teeth of the gears.

According to the present disclosure, there is provided a robot for inspecting pipelines, the robot capable of controlling motions of a connector so as to cross the obstacles on the movement path.

Furthermore, according to the present disclosure, a robot arm may approach pipelines such that the main body of the robot may contact the pipelines, and the robot arm may distance away from the pipelines such that the main body may be distanced from the pipelines.

Herein, it is possible to control the robot arm that contacts the pipelines such that the robot may move or rotate around the pipelines.

Furthermore, the robot arm may be arranged at both sides of the pipelines, thereby improving the adhesiveness to the pipelines.

Herein, a sensor may be distanced from the pipelines during a motion, so that it is prevented from being damaged due to any contact with obstacles.

In addition, a non-destructive test (NDT) may be conducted so as to prevent the pipelines from being damaged.

Herein, the connector consists of a four bar link, and may thus restrict the movement of the main body when crossing obstacles.

Furthermore, it is possible to reduce the size of a driver for applying power to a gear by increasing an output torque using the gear part.

BRIEF DESCRIPTION OF THE DRAWINGS

Throughout the drawings and the detailed description, unless otherwise described, the same drawing reference numerals will be understood to refer to the same elements, features, and structures. The relative size and depiction of these elements may be exaggerated for clarity, illustrating, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Figure 1:
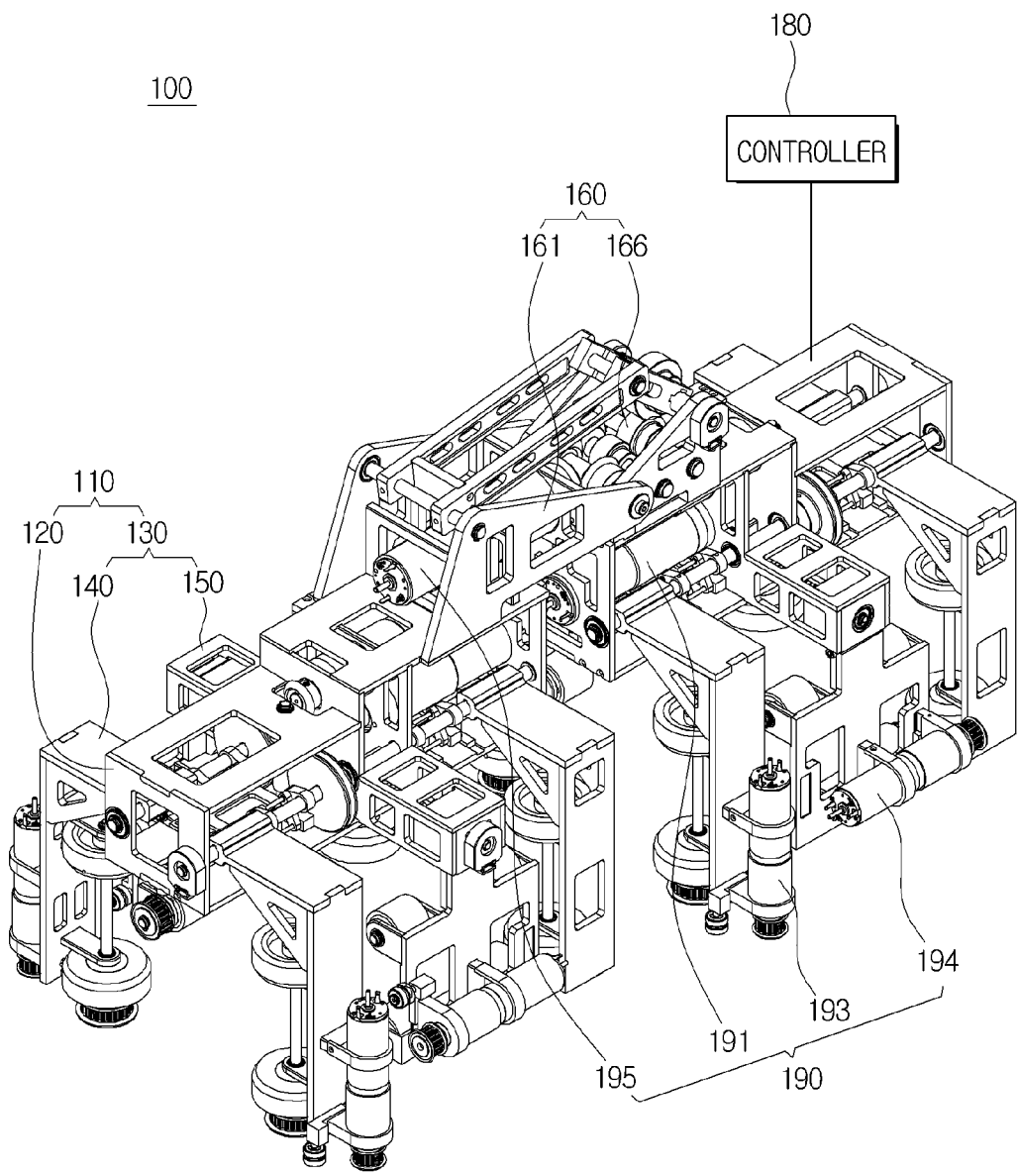
FIG. 1 is a schematic skewed view of a robot for inspecting pipelines according to an exemplary embodiment of the present disclosure.
Figure 2:
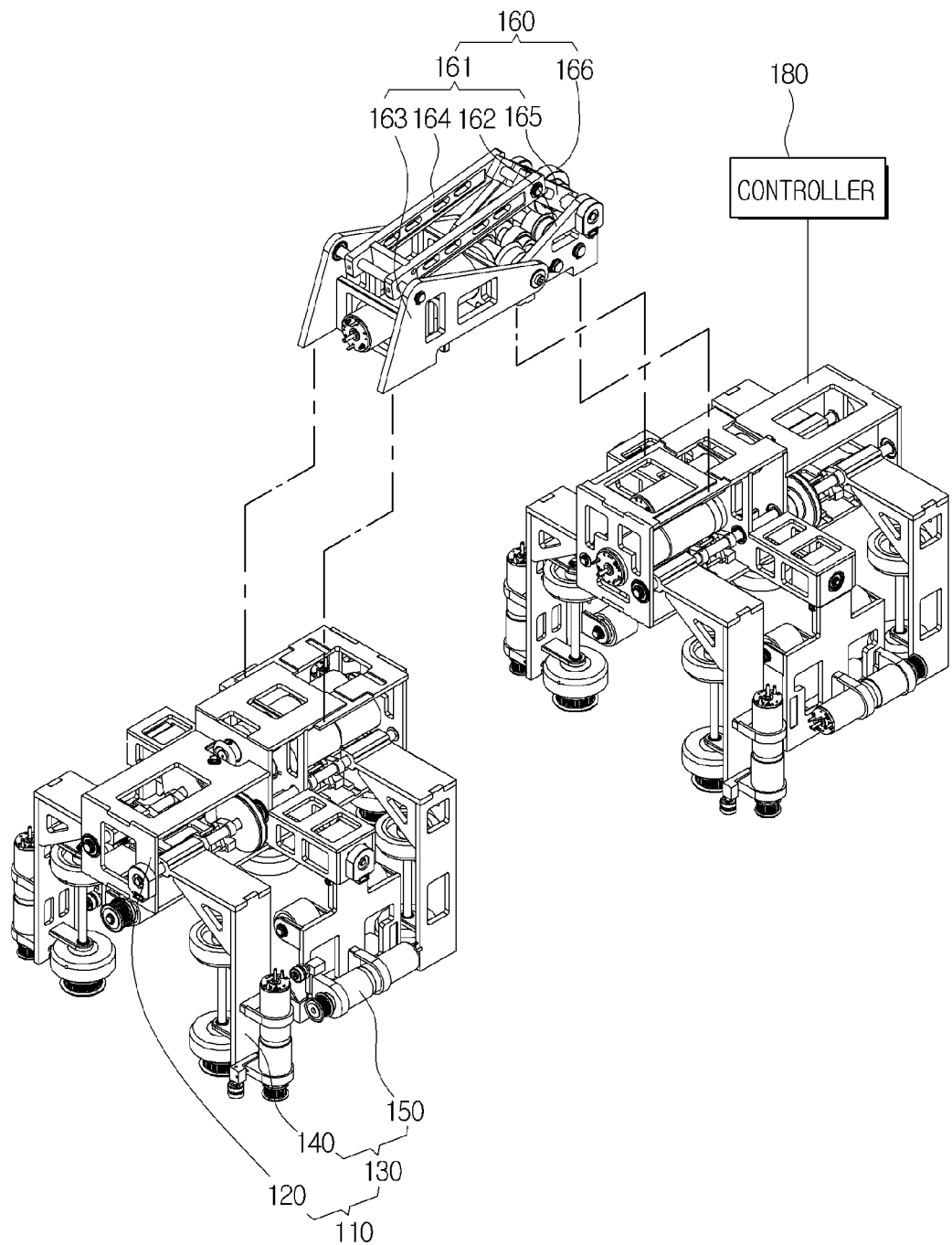
FIG. 2 is a schematic exploded skewed view of a robot for inspecting pipelines of FIG. 1.

FIG. 1 is a schematic skewed view of a robot for inspecting pipelines according to an exemplary embodiment of the present disclosure, and FIG. 2 is a schematic exploded skewed view of a robot for inspecting pipelines of FIG. 1.

With reference to FIG. 1 or FIG. 2, the robot 100 for inspecting pipelines according to an exemplary embodiment of the present disclosure is capable of easily crossing points where obstacles such as curved or branch pipes are formed. Such a robot 100 for inspecting pipelines according to an exemplary embodiment of the present disclosure comprises a body part 110, connector 160, sensor 170, controller 180, and driver 190.

The body part 110 plays the role of a main frame of the robot 100 for inspecting pipelines according to an exemplary embodiment of the present disclosure. Such a body part 110 comprises a body 120 and a robot arm 130.

Figure 3:
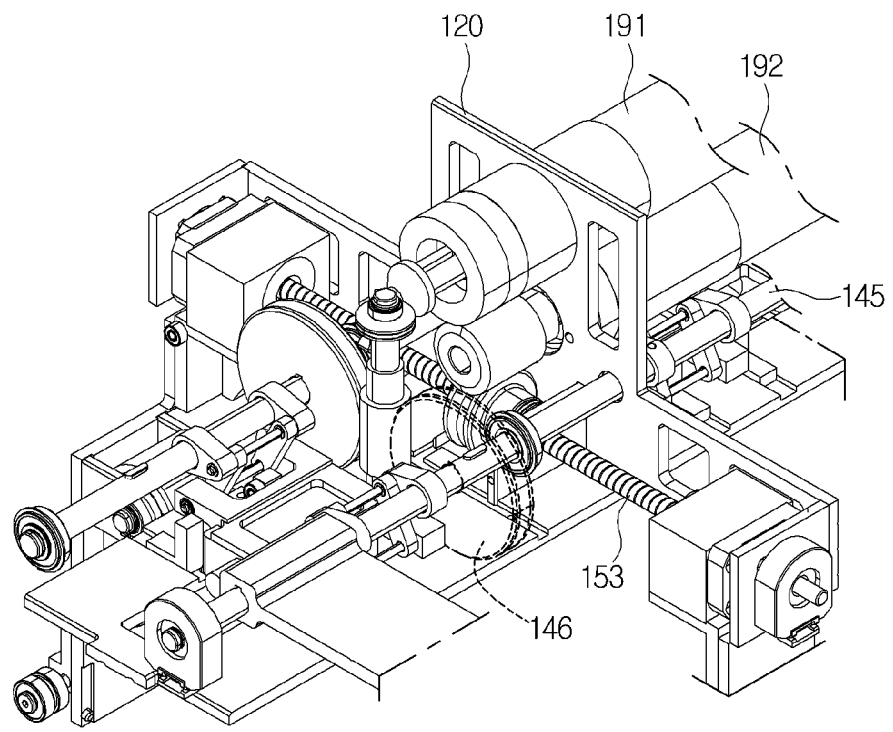
FIG. 3 is a schematic exploded skewed view illustrating the interlocked operation relationship inside a body of a robot for inspecting pipelines.

FIG. 3 is a schematic exploded skewed view illustrating the relationship of interlocked operation inside a body of a robot for inspecting pipelines.

With reference to FIG. 3, the body 120 is the main body where there is installed a robot arm 130 that will be explained hereinbelow and a driver 190 configured to apply power to the robot arm 130 so that the robot arm 130 either contacts or is distanced from the pipelines 105.

Figure 4:
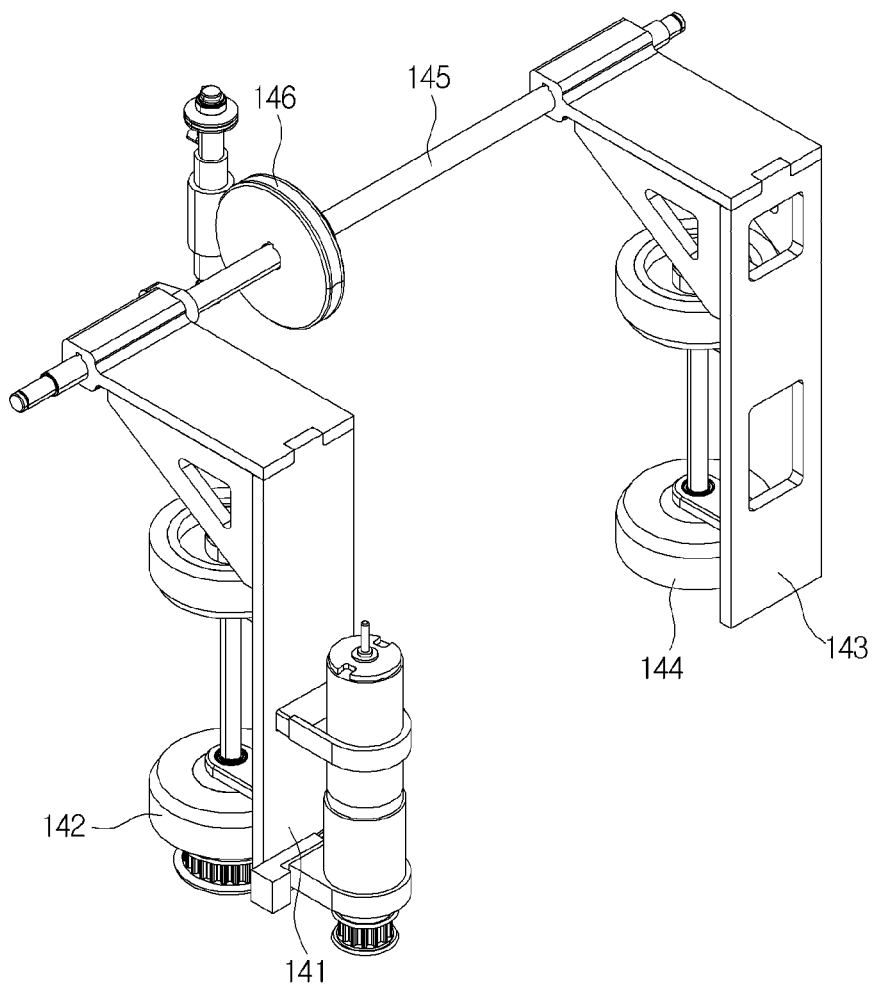
FIG. 4 is a schematic skewed view of a first robot arm of a robot for inspecting pipelines of FIG. 1.
Figure 5:
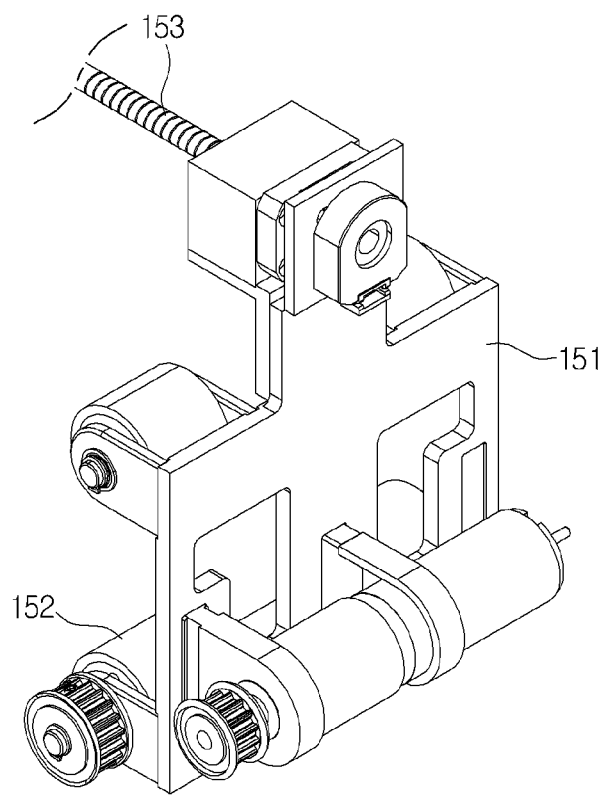
FIG. 5 is a schematic skewed view of a second robot arm of a robot for inspecting pipelines of FIG. 1.
Figure 6:
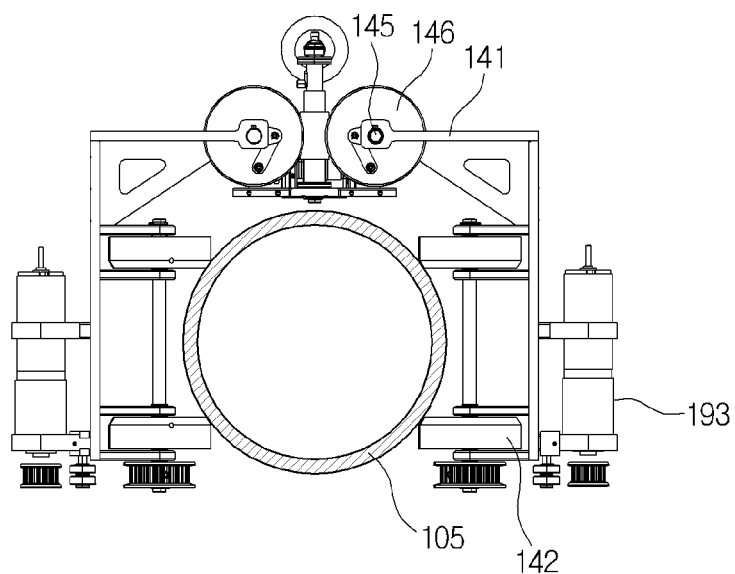
FIGS. 6 and 7 are schematic cross-sectional views of a first robot arm of a robot for inspecting pipelines of FIG. 1 being distanced from the pipelines.
Figure 7:
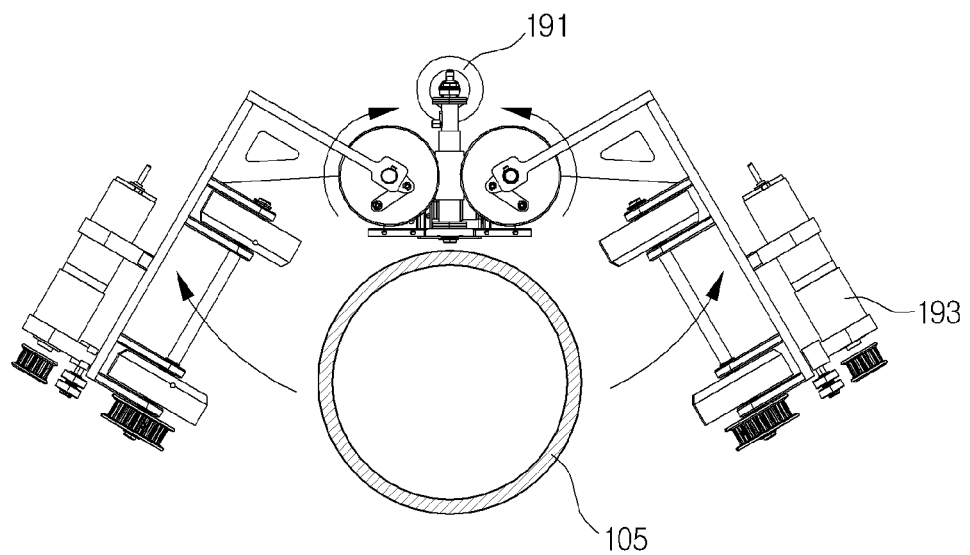
Figure 8:
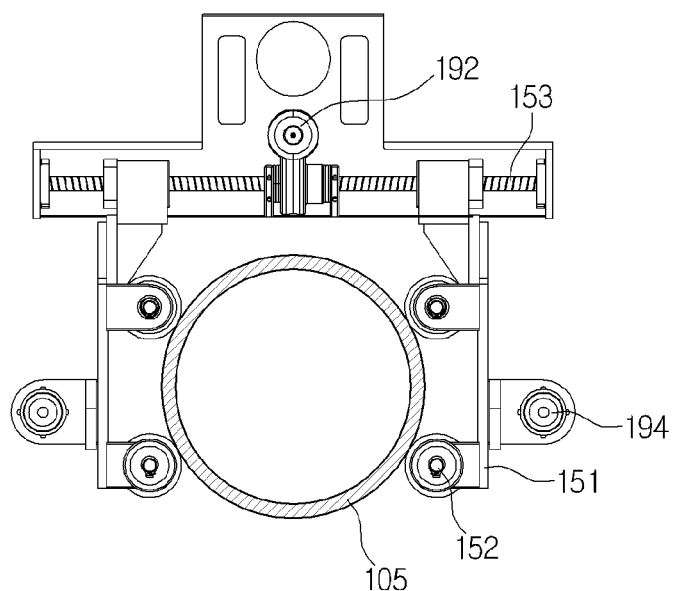
FIGS. 8 and 9 are schematic cross-sectional views of a second robot arm of a robot for inspecting pipelines of FIG. 1 being distanced from the pipelines.
Figure 9:
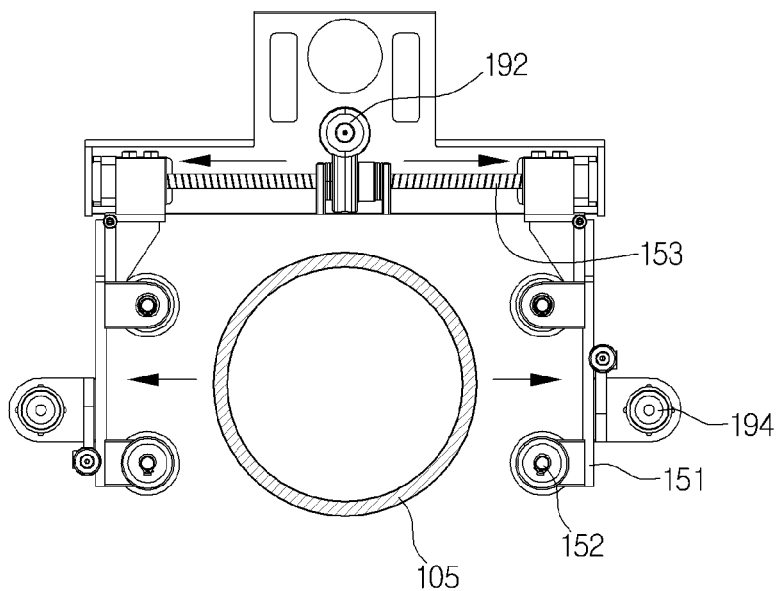

FIG. 4 is a schematic skewed view of a first robot arm of a robot for inspecting pipelines of FIG. 1, FIG. 5 is a schematic skewed view of a second robot arm of a robot for inspecting pipelines of FIG. 1, FIGS. 6 and 7 are schematic cross-sectional views of a first robot arm of a robot for inspecting pipelines of FIG. 1 being distanced from the pipelines, and FIGS. 8 and 9 are schematic cross-sectional views of a second robot arm of a robot for inspecting pipelines of FIG. 1 being distanced from the pipelines.

With reference to FIGS. 4 to 9, the robot arm 130 is configured to encircle the pipeline 105 and make the robot 100 for inspecting pipelines according to an exemplary embodiment of the present disclosure perform a straight line motion along the pipeline 105 or perform a rotating motion around the outer circumference of the pipeline 105. The robot arm 130 comprises a first robot arm 140 configured to guide the robot 100 for inspecting pipelines to perform a straight line motion, and a second robot arm 150 configured to guide the robot 100 for inspecting pipelines to perform a rotating motion.

Furthermore, the robot arm 130 is provided as a pair of robot arms at both sides of the pipeline 105 so that the robot 100 for inspecting pipelines configured to inspect the pipeline 105 as it moves on the exterior of the pipeline 105 maintains its contact with the pipeline 105. The pair of robot arms may be arranged to face each other.

The first robot arm 140 guides the robot 100 for inspecting pipelines to perform a straight line motion along the longitudinal direction of the pipeline 105. The first robot arm 140 comprises a first main robot arm member 141, first main motion part 142, first auxiliary robot arm member 143, first auxiliary motion part 144, connecting axis 145, and worm wheel 146. Herein, the first main motion part 142 and the first auxiliary motion part 144 are called a first motion part which is desirably a wheel.

The first main robot arm member 141 receives power and moves the robot 100 for inspecting pipelines along the pipeline 105. That is, on the first main robot arm member 141, the first main motion part 142 disposed such that it may rotate along the longitudinal direction of the pipeline is provided between the pipeline 105 and the first main robot arm member 141, and moves the robot 100 for inspecting pipelines, with a wheel 142 for the first main robot arm contacting the pipeline.

The first auxiliary robot arm member 143 is for stably guiding a movement path of the robot 100 for inspecting pipelines moved by the first main robot arm member 141. On the first auxiliary robot arm member 143, a first auxiliary motion part 144 disposed such that it may rotate along the longitudinal direction of the pipeline is provided between the pipe 105 and the first main robot arm member 143, and rotates in response to the rotation of the first main motion part 142 with the first auxiliary motion part 144 contacting the pipeline 105.

The connection axis 145 is connected with the first main robot arm member 141 and the first auxiliary robot arm member 143, and enables the first main robot arm member 141 and the first auxiliary robot arm member 143 to approach the pipeline 105 or distance from the pipeline 105.

That is, by the rotation of the connection axis 145, the first main robot arm member 141 and the first auxiliary robot arm member 143 rotate around the connection axis 145. Furthermore, according to an exemplary embodiment of the present disclosure, when the connection axis 145 rotates counterclockwise when seen from the front side of the first body part 110a, the first main robot arm member 141 and the first auxiliary robot arm member 143 may distance away from the pipeline 105, and when the connection axis 145 rotates clockwise, the first main robot arm member 141 and the first auxiliary robot arm member 143 may approach the pipeline 105. However, there is no limitation thereto.

The worm wheel 146 is provided such that it is inserted into the connection axis 145, and is rotated by the rotation of the connection axis 145. The worm wheel 146 is relevant to the operation of the sensor 170 to be explained hereinbelow, and thus more detailed explanation about the worm wheel 146 will be made hereinbelow.

The second robot arm 150 guides the robot 100 for inspecting pipelines such that the robot 100 may perform a rotating motion along the outer circumference surface of the pipeline 105. On the second robot arm 151, the second motion part 152 disposed such that it may rotate along the outer circumference surface of the pipeline 105 is provided between the second robot arm member 151 and the pipeline 105.

Furthermore, there is provided a ball screw 153 that connects the pair of second robot arms 150, and by the rotation of the ball screw 153, the pair of second robot arms 150 either approach each other or distance from each other.

Meanwhile, in the robot 100 for inspecting pipelines according to an exemplary embodiment of the present disclosure, the aforementioned body part 110 comprises a first body part 110a and a second body part 110b connected to each other along the longitudinal direction of the pipeline 105. If the body part 110 were just one piece, although it may be possible to perform a straight motion or rotating motion, it would be difficult to cross obstacles. Therefore, it is desirable that the body part 110 has two pieces each of which may cross the obstacles successively.

Furthermore, the first robot arm 140 and the second robot arm 150 may be formed differently from the above, and thus there is no limitation thereto.

Figure 10:
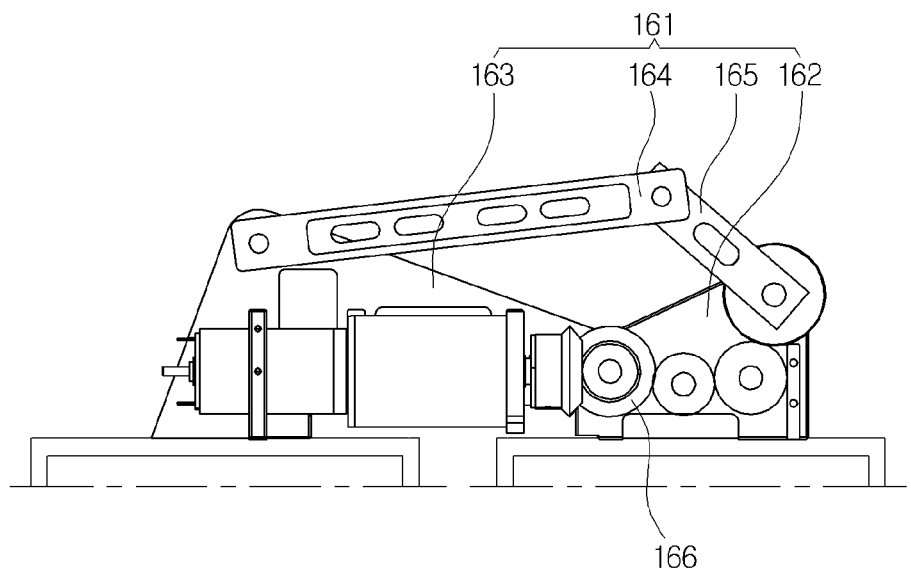
FIG. 10 is a schematic cross-sectional view of a connector of a robot for inspecting pipelines of FIG. 1.

FIG. 10 is a schematic cross-sectional view of a connector of a robot for inspecting pipelines of FIG. 1. With reference to FIG. 8, the connector 160 comprises a link 161 and a gear part 166, and connects the two pieces of the body part 110.

The link 161 restricts the motion of the body part 110 such that the robot 100 for inspecting pipelines may maintain the condition capable of crossing obstacles. The link 161 comprises a first link 162, second link 163, third link 164, and fourth link 165.

Herein, the first link 162 is provided on the upper side of the first body part 110a, and the second link 163 is provided on the upper side of the second body part 110b and is connected to the first link 162. The third link 164 is connected to the second link 162 and fourth link 165, and the fourth link 165 is connected with the first link 162 and the third link 164.

In addition, one of the first link 162 and the second link 163 installed in the first body part 110a or second body part 110b is secured and lifts the first body part 110a or second body 11b from the first link 162 or second link 163. For example, in the case of lifting the second body part 110b, the first link 162 installed in the first body part 110a is secured and the second link 163 rotates counterclockwise. The rotation by the second link 163 is restricted by the third link 164 and the fourth link 165.

Herein, the length of the first link 162, second link 163, third link 164, and fourth link 165 may be set differently depending on circumstances.

The gear part 166 is a configuration of which the rotating speed decreases but the output torque increases as power input into the gear part 166 goes through a plurality of gears. That is, the gear part 166 generates a high output with small power that has been input.

In order to lift the body part 110 through the aforementioned link 161, a power greater than the weight of the body part 110 must be input into the link 161. Herein, the size of the device must be big in order to input the power without any device. Therefore, if the rotating speed can be reduced through the gear part 166 and the output torque can be amplified to exceed the input torque of the power input, it may be possible to reduce the size of the connector 160.

Meanwhile, regarding the gear teeth of the gear part 166, it is necessary that at least the number or size of the gear teeth increases as it gets closer to the output side so as to increase the torque. That is, it is desirable that both the number and size of the gear teeth increase as it gets closer to the output side, but there is no limitation thereto.

In addition, in the robot 100 for inspecting pipelines according to an exemplary embodiment of the present disclosure, the gear part 166 has 4 gears, where in gear 1 and gear 2, the number or size of the gear teeth is different between their input side and output side. That is, in gear 1, the number or size of the gear teeth at the input side is different from that at the output side. In gear 1, it is desirable that the number and size of the gear teeth that receives power is greater than that of the gear teeth that transmits power to gear 2, and the smaller the number and size of the gear teeth that transmit power to gear 2, the better.

Meanwhile, in gear 2, it is desirable that the number and size of the gear teeth that transmits power from gear 1 to gear 2 is greater than the number and size of the gear teeth that transmits power from gear 1 to gear 2, and in gear 2, the smaller the number and size of the gear teeth that transmit power to gear 3, the better.

That is, by forming a configuration where gears engage their adjacent gears, it is sufficient to increase the output torque, but this would increase the size of the gear part 166, consequently increasing the size of the connector 160. Accordingly, in the robot 100 for inspecting pipelines according to an exemplary embodiment of the present disclosure, the aforementioned method was adopted to reduce the size of the connector 160, but there is no limitation thereto.

Figure 11:
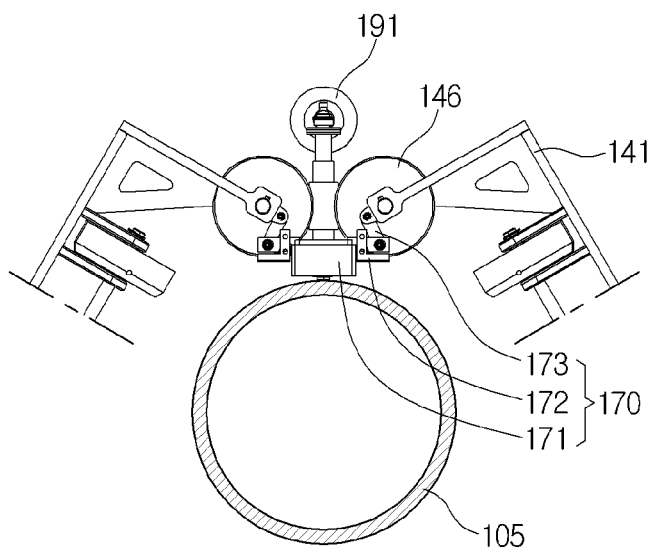
FIGS. 11 and 12 are schematic cross-sectional views of a sensor of a robot for inspecting pipelines of FIG. 1 being interlocked with a first robot arm and distanced from the pipelines.
Figure 12:
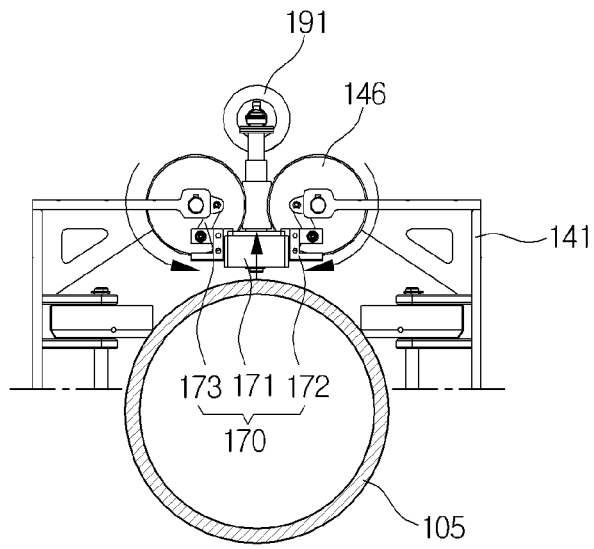

FIGS. 11 and 12 are schematic cross-sectional views of a sensor of a robot for inspecting pipelines of FIG. 1 being interlocked with a first robot arm and distanced from the pipelines.

With reference to FIGS. 11 and 12, the sensor 170 comprises a sensor 171, sensor guide 172, and five bar link 173, and is configured to inspect the condition of the pipelines.

The sensor 171 inspects the condition of the pipelines, and according to an exemplary embodiment of the present disclosure, the sensor 171 may be an electromagnetic acoustic transducer (EMAT) for performing a non-destructive test (NDT), but there is no limitation thereto.

The sensor guide 172 is provided on both sides of the sensor 171 to guide the motion of the sensor 171. The sensor guide 172 is provided with a five bar link 173 that will be explained hereinbelow. The sensor guide 172 guides the sensor 171 such that the sensor 171 move in a central or radial direction while limiting the movement of the five bar link 173.

The fifth bar link 173 is connected to the sensor guide 172, and is connected to the worm wheel 146 so as to guide the sensor 171 such that the sensor 171 may move in an interlocked manner with the rotation of the connection axis 145. That is, when the first robot arm 140 is distanced away from the pipeline 105, in other words, when the second robot arm 150 approaches the pipeline 105, the sensor 171 also operates to approach the pipeline 105.

That is, when the first robot arm 140 rotates away from the pipeline 105, that is in the counterclockwise direction, the connection axis 145 and worm wheel 146 also rotate counterclockwise, the five bar link 173 of which one end is secured to the worm wheel 146 rotates along the worm wheel 146, and the sensor 171 moves towards the pipeline 105 by the sensor guide 172.

With one of the first body part 110a and the second body part 110b secured, the controller 180 controls the connector 160 to lift the other body part 110 and cross the obstacle.

In addition, at the same time of controlling the connector 160, the controller 180 controls the first robot arm 140 and second robot arm 150 so as to control whether or not the first robot arm 140 and second robot arm 150 should contact the pipeline 105.

The driver 190 comprises a first motor 191, second motor 192, third motor 193, fourth motor 194, and fifth motor 195, and the driver 190 applies power to the robot 100 for inspecting pipelines.

The first motor 191 is installed in the body 120 and is configured to transmit power to the first robot arm 140 so that the first robot arm 140 may perform a motion of approaching the pipeline 105 or distance away from the pipeline 105. The second motor 192 is installed in the body 120 and is configured to transmit power to the second robot arm 150 so that the second robot arm 140 may perform a motion of approaching the pipeline 105 or distance away from the pipeline 105.

In addition, the first motor 193 is installed in the first main robot arm member 141 and is configured to transmit power to the first main motion part 142, and the fourth motor 194 is installed in the second robot arm 150 and is configured to transmit power to the second motion part 152, and the fifth motor 195 is provided in the connector 160 and is configured to apply power to the connector 160 such that the connector 160 may lift the first body part 110a or second body part 110b.

Meanwhile, the third motor 193 or fourth motor 194 transmits power to the first main motion part 142 or second motion part 152 by the belt(not illustrated), but there is no limitation thereto.

Hereinbelow is explanation on an operation regarding a straight motion, rotating motion and motion of crossing of obstacles in a robot for inspecting pipelines aforementioned according to an exemplary embodiment of the present disclosure.

In the case where a robot 100 for inspecting pipelines according to an exemplary embodiment of the present disclosure performs a straight motion along the pipeline 105, power is applied from the first motor 191 and second motor 192 so that the first robot arm 140 contacts the pipeline 105 and the second robot arm 150 is distanced away from the pipeline 105. That is, for the robot 100 for inspecting pipelines to perform a straight motion, the first robot arm 140 must contact the pipeline 105. This is because, since the second motion part 152 of the second robot arm 150 is provided such that it is rotatable along the outer circumference surface of the pipeline 105, when the second motion part 152 contacts the pipeline 105, the straight line motion of the robot for inspecting pipelines is interrupted.

Herein, once the first robot arm 140 contacts the pipeline 105, power is applied from the third motor 193 to the first main motion part 144, enabling the robot for inspecting pipelines to perform a straight line motion.

Such a straight line motion is performed in the case where the robot 100 for inspecting the pipelines move along the pipeline 105, but there is no limitation thereto.

Figure 13:
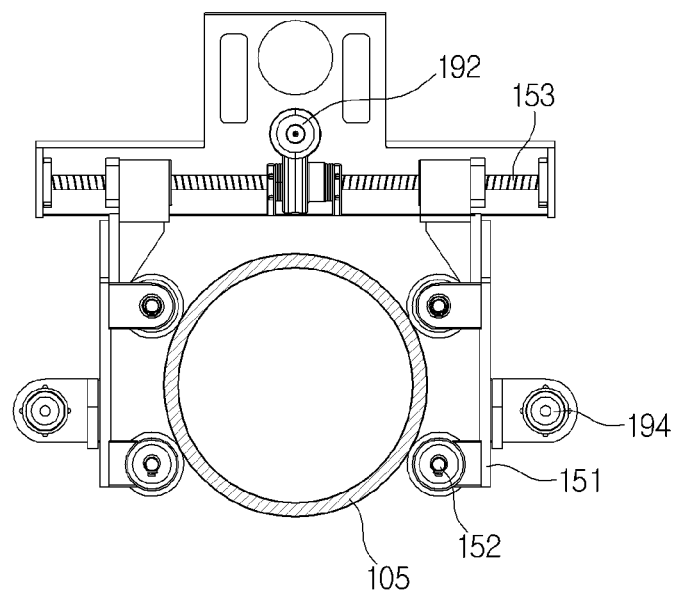
FIGS. 13 and 14 are schematic cross-sectional views of a robot for inspecting pipelines of FIG. 1 performing a rotating motion using a second robot arm.
Figure 14:
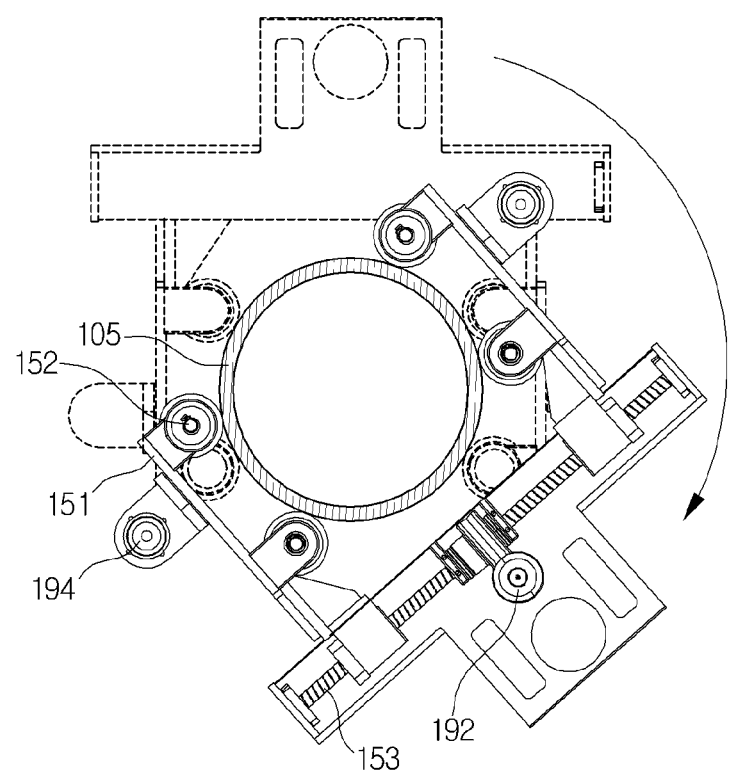

FIGS. 13 and 14 are schematic cross-sectional views of a robot for inspecting pipelines of FIG. 1 performing a rotating motion using a second robot arm.

With reference to FIGS. 13 and 14, in the case where the robot 100 for inspecting pipelines according to an exemplary embodiment of the present disclosure performs a rotating motion along the outer circumference surface of the pipeline 105, power is applied from the first motor 191 and second motor 192 so that the first robot arm 140 may be distanced away from the pipeline 105 and the second robot arm 150 may approach the pipeline.

That is, for the robot for inspecting the pipelines to perform a rotating motion, only the second robot arm 150 must contact the pipeline 105, which is because since the first main motion part 152 of the first robot arm 140 is provided such that it is movable along the pipeline 105, when the first main motion part 142 contacts the pipeline 105, the rotating motion of the robot for inspecting pipelines is interrupted.

Herein, once the second robot arm 150 contacts the pipeline 105, power is applied from the fourth motor 194 to the second motion part 152, enabling the robot for inspecting pipelines to perform a rotating motion.

Such a rotating motion is performed only when the robot 100 for inspecting pipelines perform an inspection. That is, with the sensor 170 contacting the pipeline 105, when the robot rotates, the sensor 170 is also rotated thereby inspecting the pipeline along the circumference direction. However, such a rotating motion is not limited to performing inspections, but may well also be performed to avoid obstacles when there is an obstacle that is difficult to pass such as a wall.

With reference to FIGS. 11 and 12, in the case where the sensor 170 performs a motion of approaching the pipeline 105, the first robot arm 140 receives power from the first motor 191 through the connection axis 145. That is, the connection axis 145 rotates in an interlocked manner with the first motor 191, thereby also rotating the worm wheel 146 inserted into the connection axis 145. When the connection axis 145 and worm wheel 146 rotate counterclockwise, the five bar link 173 of the sensor 170 of which one end is secured to the worm wheel 146 rotates along the worm wheel 146, and the sensor 171 is moved towards the pipeline 105 by the sensor guide 172.

As such, it is possible to make the sensor 170 move using the first motor 191 without having to add a driver, thereby reducing the size of the robot 100 for inspecting pipelines.

However, unlike the robot 100 for inspecting pipelines according to an exemplary embodiment of the present disclosure, the first robot arm 140 may be connected to the ball screw 153, the second robot arm 150 may be connected to the connection axis 145, in which case the movement of the sensor 170 is determined in an interlocked manner with the motion of the second robot arm.

Figure 15:
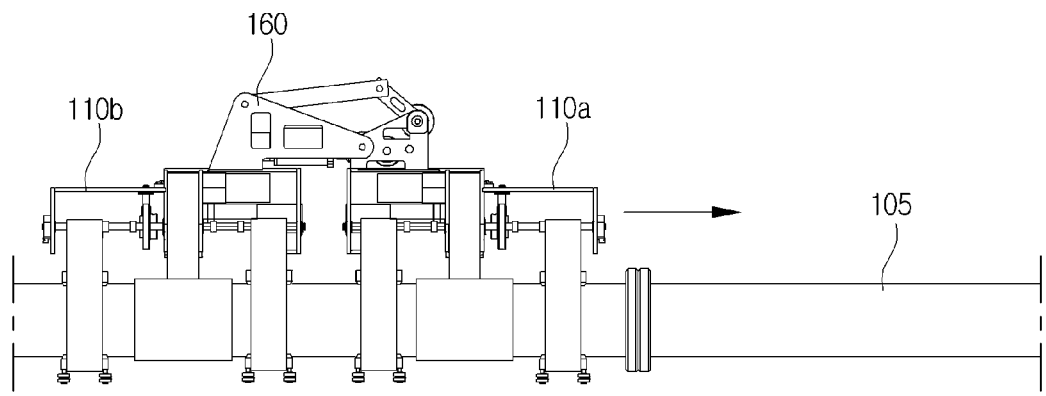
FIG. 15 is a schematic front view of a robot for inspecting pipelines of FIG. 1 that moved until approaching an obstacle.
Figure 16:
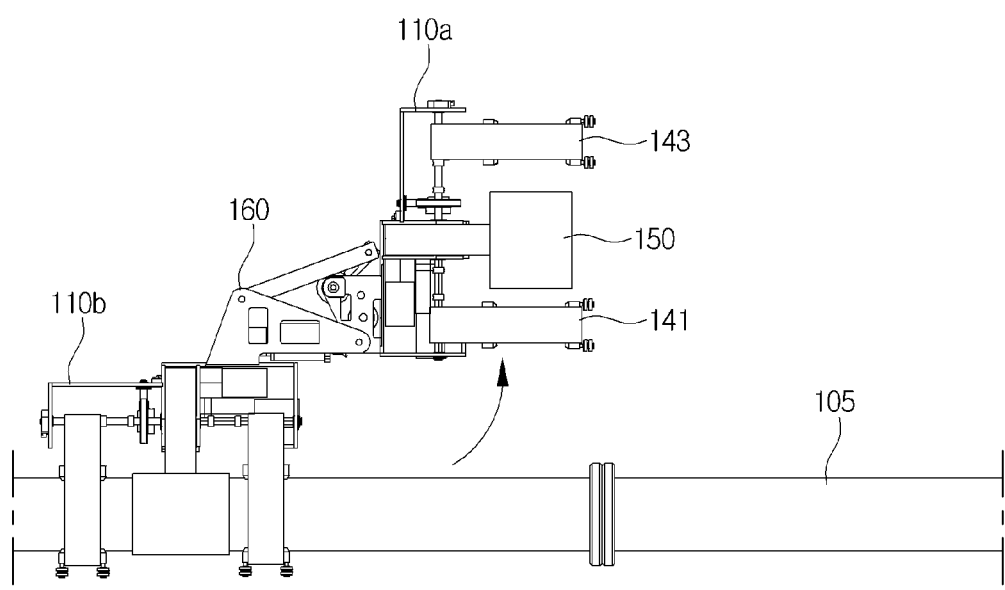
FIG. 16 is a schematic front view of a robot for inspecting pipelines of FIG. 1, the robot lifting a first body part to cross an obstacle.
Figure 17:
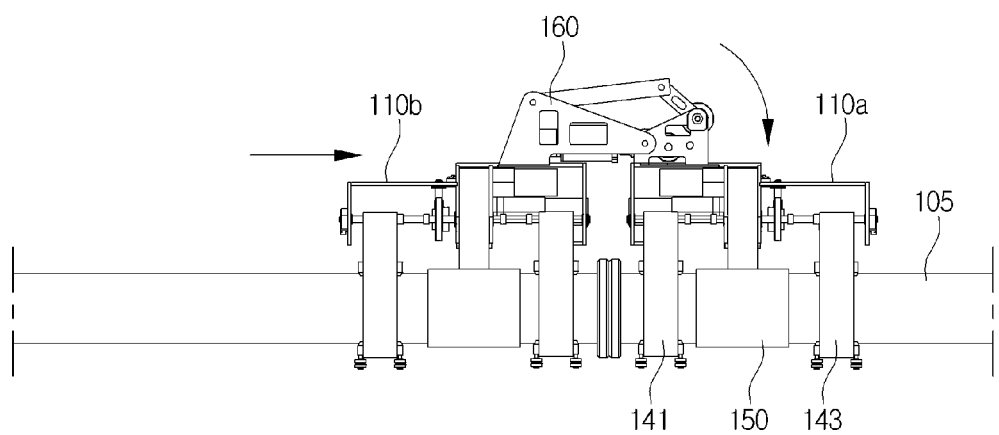
FIG. 17 is a schematic front view of a first body part of a robot for inspecting pipelines of FIG. 1, wherein the first body part has crossed an obstacle.
Figure 18:
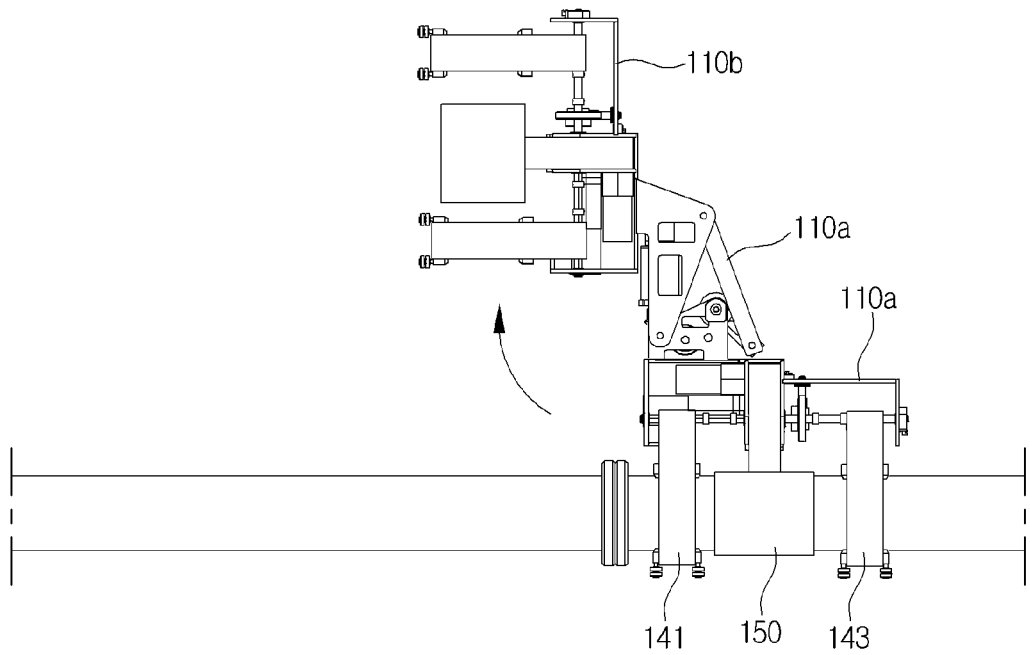
FIG. 18 is a schematic front view of a robot for inspecting pipelines of FIG. 1, the robot lifting a second body part to cross an obstacle.
Figure 19:
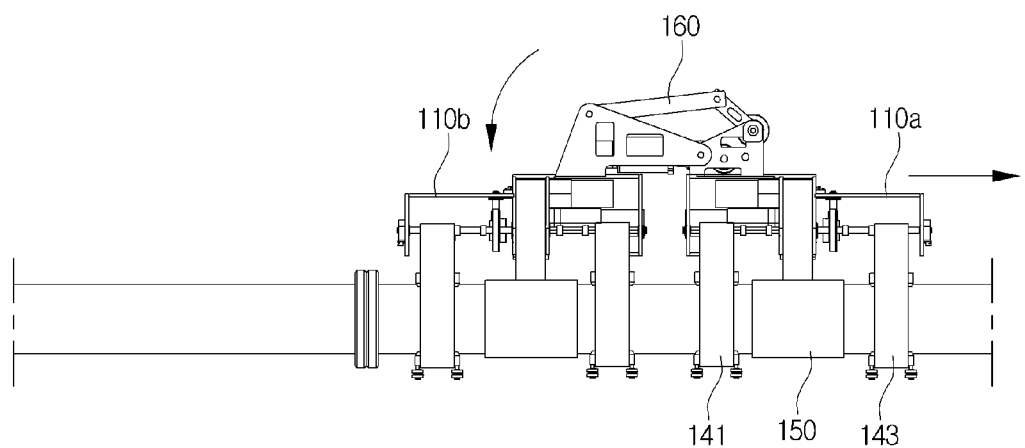
FIG. 19 is a schematic front view of a robot for inspecting pipelines of FIG. 1, wherein a second body part has crossed an obstacle.

FIG. 15 is a schematic skewed view of a second robot arm of a robot for inspecting pipelines of FIG. 1, FIG. 16 is a schematic front view of a robot for inspecting pipelines of FIG. 1, the robot lifting a first body to cross an obstacle, FIG. 17 is a schematic front view of a first body of a robot for inspecting pipelines of FIG. 1, wherein a first body has crossed an obstacle, FIG. 18 is a schematic front view of a robot for inspecting pipelines of FIG. 1, the robot lifting a second body to cross an obstacle, and FIG. 19 is a schematic front view of a robot for inspecting pipelines of FIG. 1, wherein a second body has crossed an obstacle.

With reference to FIGS. 15 to 19, in the case where the robot 100 for inspecting pipelines according to an exemplary embodiment of the present disclosure performs a motion of crossing an obstacle such as a curved or branch pipe on the pipeline 105, first of all, the second body part 110b is secured to the pipeline 105. The movement of the second body part 110b may be secured as both the first robot arm 140 and second robot 150 contact the pipeline 105, but there is no limitation thereto.

After the second body part 110b is secured, the first robot arm 140 and the second robot arm 150 of the first body part 110a are distanced away from the pipeline 105.

When power is applied from the fifth motor 195 with the first robot arm 140 and the second robot arm 150 of the first body part 110a distanced away from the pipeline 105, the first body part 110a is lifted 105 from the pipeline 105 by the gear 162, and the first body part 110a moves up to the point restricted by the link 161.

After the first body part 110a is moved up to the maximum point, the second body part 110b performs a straight line motion to move up to the range where an obstacle is located in the space formed between the first body part 110a and the second body part 110b.

When the movement is completed, by the fifth motor 195 the first body part 110a is placed near the pipeline 105, and the first body part 110a is secured to the pipeline 105. In order to make the first robot arm 140 and second robot arm 150 contact the pipeline 105 at the same time, it is possible to secure the first body part 110a to the pipeline 105, but there is no limitation thereto.

When the first body part 110a is secured, the second body part 110b is lifted from the pipeline 105, and the first body part 110a is moved up to the point where the second body part 110b completely crosses the obstacle. This is the same as the process where the first body part 110a is lifted and an obstacle is crossed, and thus detailed explanation is omitted.

Figure 20:
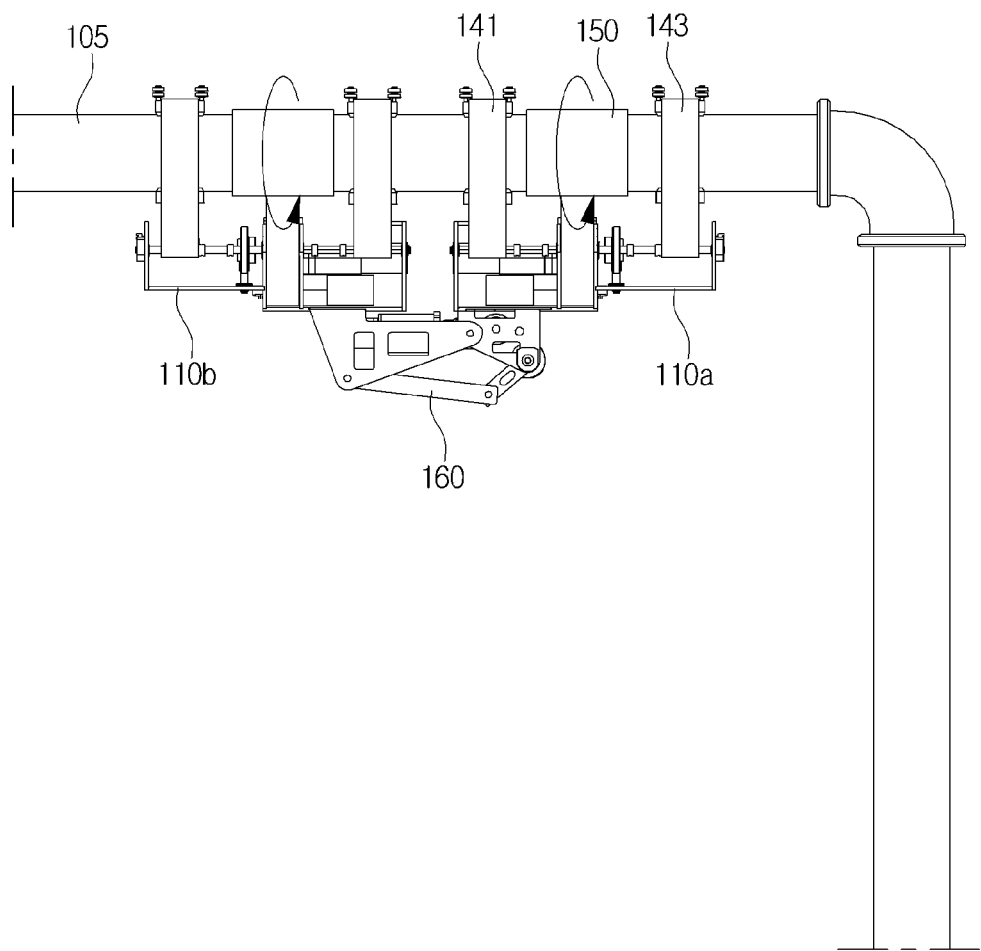
FIG. 20 is a schematic front view of a robot having rotated an outer circumference of a pipeline for a robot for inspecting pipelines of FIG. 1 to cross a curved duct.
Figure 21:
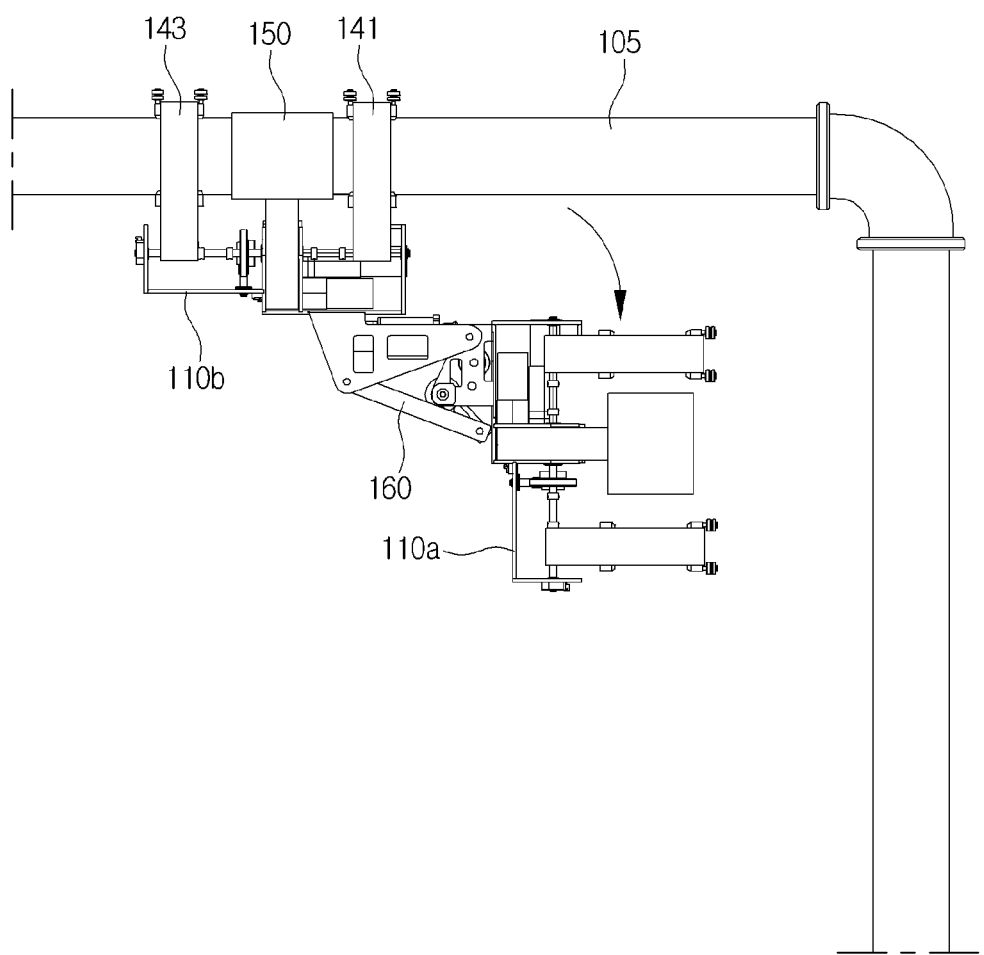
FIG. 21 is a schematic front view of a robot for inspecting pipelines of FIG. 1 lifting a first body part to cross a curved duct.
Figure 22:
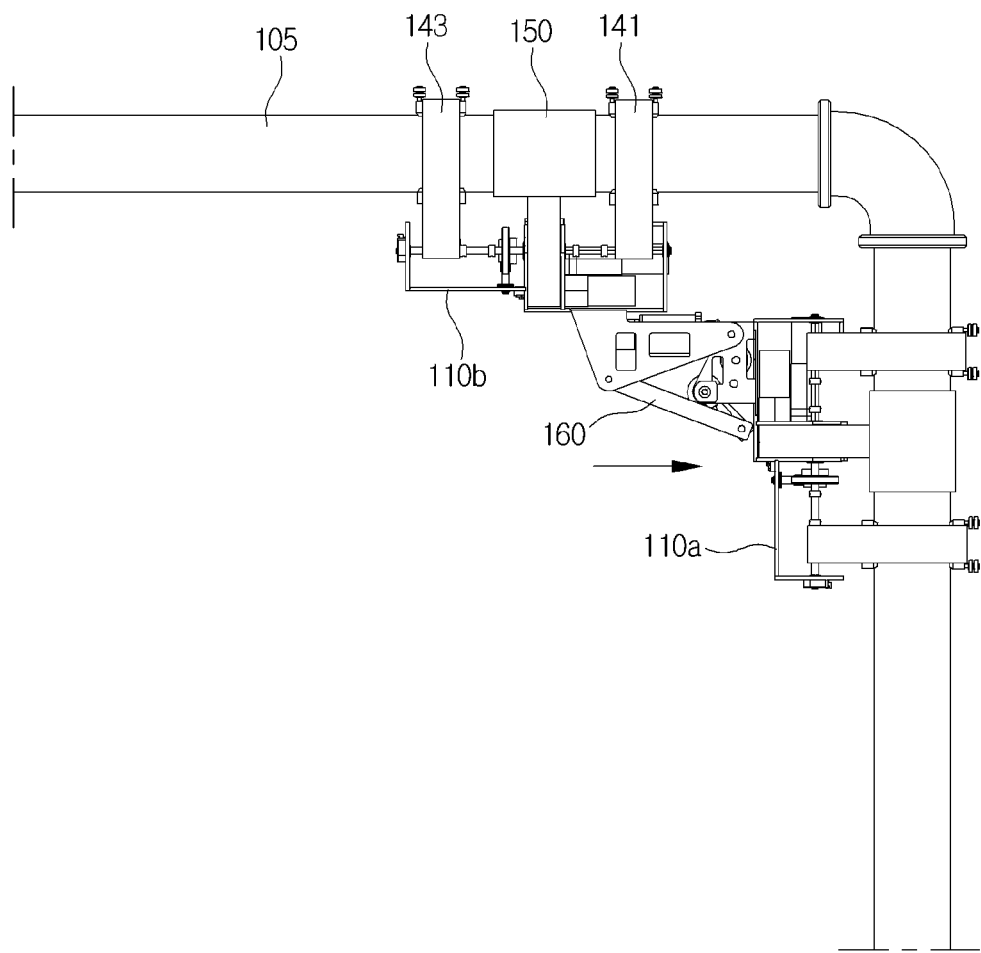
FIG. 22 is a schematic front view of a robot for inspecting pipelines of FIG. 1, wherein a first body part is mounted on a pipeline.
Figure 23:
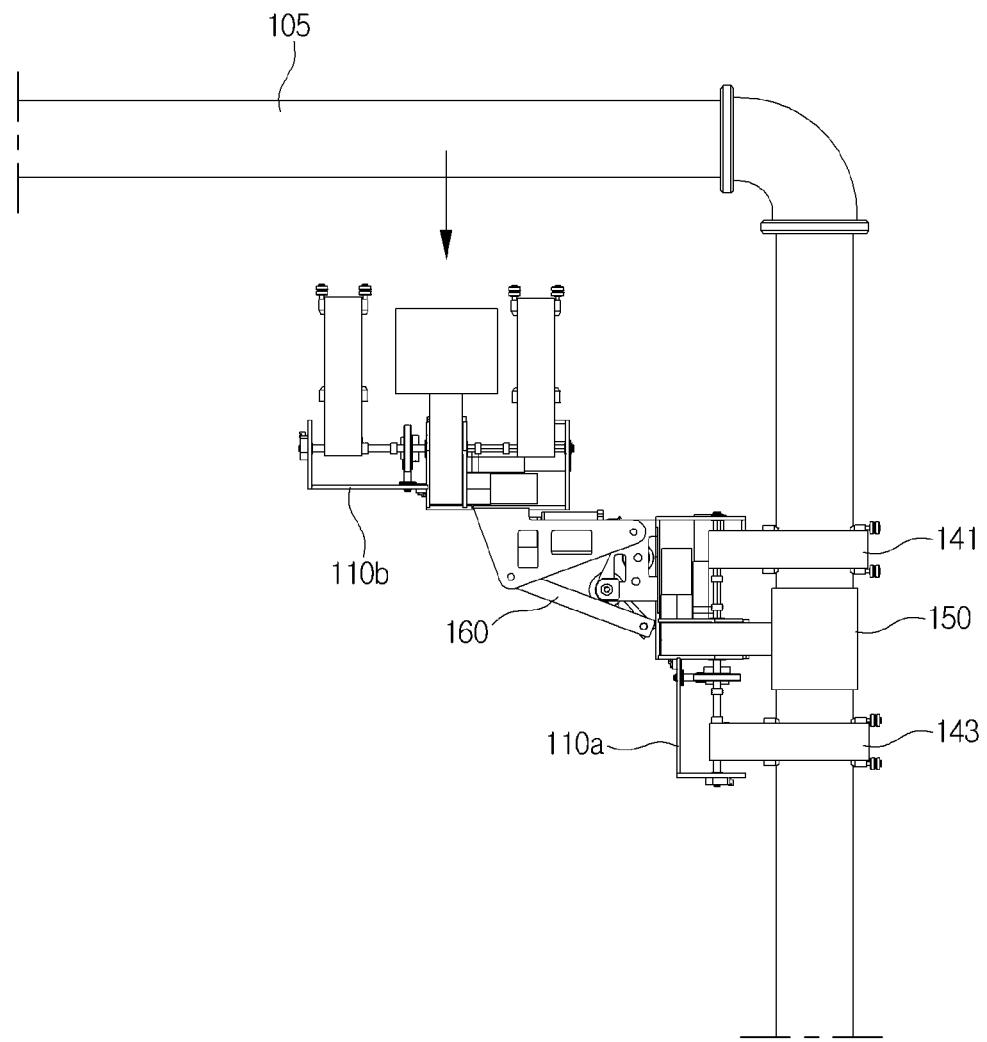
FIG. 23 is a schematic front view of a robot for inspecting pipelines of FIG. 1, wherein a second body part is distanced from a pipeline.
Figure 24:
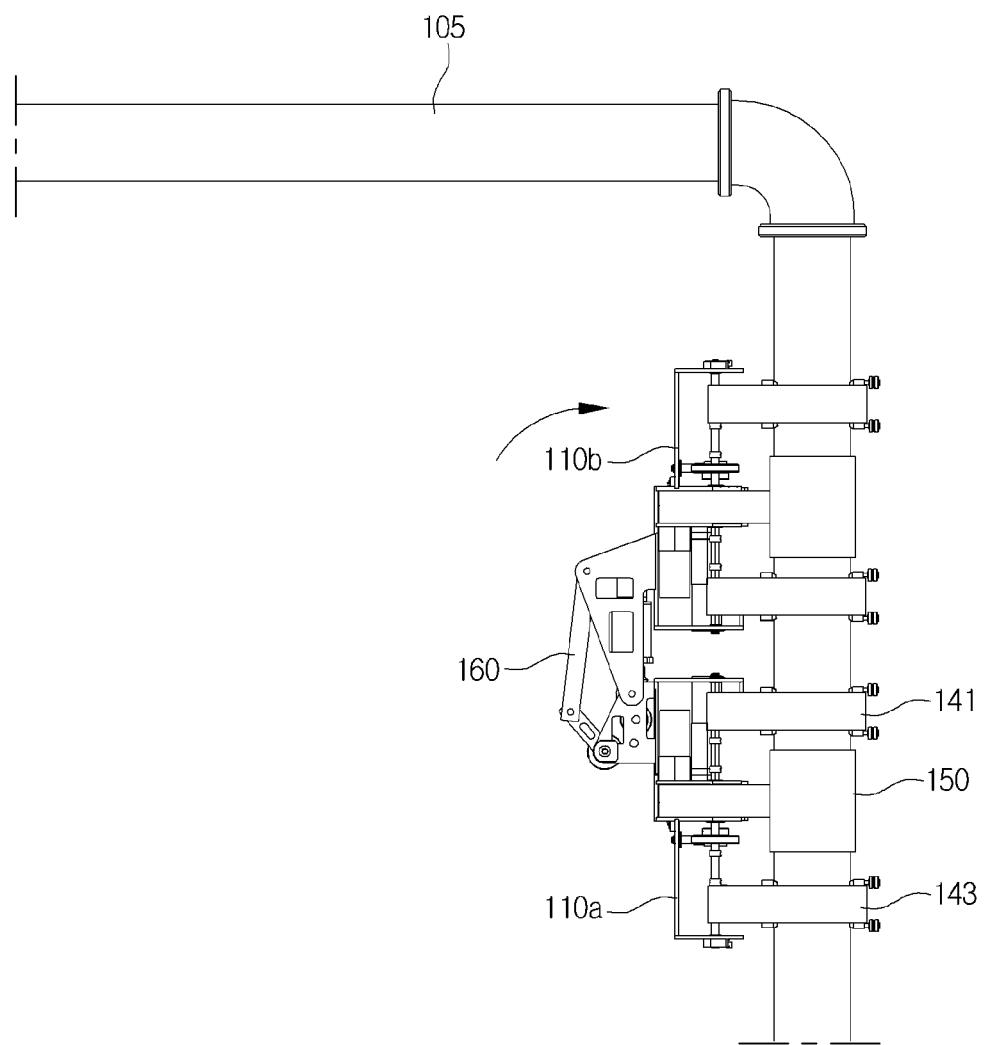
FIG. 24 is a schematic front view of a robot for inspecting pipelines of FIG. 1, wherein a first body part and a second body part both crossed a curved duct.

FIG. 20 is a schematic front view of a robot having rotated an outer circumference of a pipeline for a robot for inspecting pipelines of FIG. 1 to cross a curved duct, FIG. 21 is a schematic front view of a robot for inspecting pipelines of FIG. 1 lifting a first body part to cross a curved duct, FIG. 22 is a schematic front view of a robot for inspecting pipelines of FIG. 1, wherein a first body part is mounted on a pipeline, FIG. 23 is a schematic front view of a robot for inspecting pipelines of FIG. 1, wherein a second body part is distanced from a pipeline, and FIG. 24 is a schematic front view of a robot for inspecting pipelines of FIG. 1, wherein a first body part and a second body part both crossed a curved duct.

With reference to FIGS. 20 to 24, a robot 100 for inspecting pipelines according to an exemplary embodiment of the present disclosure rotates around an outer circumference by 180° with the robot distanced by a predetermined distance from the point where the curved duct is formed.

As in the case where the robot 100 for inspecting pipelines crosses an obstacle, the first body part 110a is lifted from the pipeline, and the first body part 110a approaches the pipeline until the first robot arm 140 and second robot arm 150 encircle the pipeline.

When the first robot arm 140 and second robot arm 150 of the first body part 110a encircle the pipeline, the first robot arm 140 and second robot arm 150 of the second body part 110b are distanced from the pipeline, and thus the robot 100 for inspecting the pipelines is moved along the pipeline.

Herein, it is desirable that the robot 100 for inspecting pipelines 100 moves until the second body part 110b passes the portion where the curved duct is formed.

Meanwhile, after the robot 100 for inspecting pipelines moves a predetermined distance, the second body part 110b approaches the pipeline, so that the first robot arm 140 and second robot arm 150 of the second body part 110b may encircle the pipeline.

That is, as the robot 100 for inspecting pipelines according to an exemplary embodiment of the present disclosure performs a straight line motion, rotating motion, and a motion of crossing obstacles, it becomes capable of moving along any time of pipeline and test the exact condition of the pipeline.

A number of examples have been described above. Nevertheless, it will be understood that various modifications may be made. For example, suitable results may be achieved if the described techniques are performed in a different order and/or if components in a described system, architecture, device, or circuit are combined in a different matter and/or replaced or supplemented by other components or their equivalents. Accordingly, other implementations are within the scope of the following claims.

DESCRIPTION OF REFERENCE NUMERALS

100: ROBOT FOR INSPECTING PIPELINES
105: PIPELINE
110: BODY PART
120: BODY
130: ROBOT ARM
140: FIRST ROBOT ARM
150: SECOND ROBOT ARM
160: CONNECTOR
170: SENSOR
180: CONTROLLER
190: DRIVER

What is claimed is:

1. A robot for inspecting pipelines as it moves along an outer surface of a pipeline, the robot comprising:
    body parts detachably provided along a longitudinal direction of the pipeline;
    a connector configured to connect adjacent body parts among the body parts, and to move one of the body parts away from the pipeline so that the body parts may cross an obstacle;
    a controller configured to control the connector to lift one of the body parts to cross the obstacle, with another one of the body parts secured to the pipeline; and
    a sensor provided in at least one body part among the body parts,
    wherein each body part comprises a plurality of robot arms,
    wherein each plurality of robot arms comprises a first robot arm configured to contact the pipeline and guide a respective body part to perform a straight line motion along the longitudinal direction of the pipeline, and a second robot arm configured to contact the pipeline and guide another respective body part to perform a rotating motion around a circumference direction of the pipeline,
    wherein the sensor is configured to contact the pipeline to inspect the pipeline, and
    wherein the sensor is interlocked with the first robot arm such that when the first robot arm moves away from the pipeline, the sensor approaches the pipeline.

2. The robot according to claim 1,
    wherein each body part comprises a body, and
    wherein each robot arm among each plurality of robot arms is attached to one of the bodies and encircles both sides of the pipeline.

3. The robot according to claim 2,
    wherein each robot arm among each plurality of robot arms is configured to perform a motion of approaching the pipeline or moving away from the pipeline.

4. The robot according to claim 1,
    wherein the first robot arm comprises a first robot arm member connected to the respective body part; and a first motion part provided between the first robot arm member and the pipeline, and rotates along a longitudinal direction of the pipeline.

5. The robot according to claim 4,
    wherein the first robot arm comprises a first main robot arm configured to receive power from outside and move the respective body part, and a first auxiliary robot arm configured to assist the first main robot arm to guide a movement direction of the respective body part.

6. The robot according to claim 1,
    wherein the second robot arm comprises a second robot arm member connected to the other respective body part; and a second motion part provided between the second robot arm member and the pipeline, and is configured to rotate around a circumference direction of the pipeline.

7. The robot according to claim 1,
    wherein the sensor is an electromagnetic acoustic transducer (EMAT) configured to perform non-destructive test (NDT).

8. The robot according to claim 1,
    wherein the connector comprises a four bar link configured to connect the adjacent body parts, and to restrict the movement of the body parts, and
    lifts a first link or second link by an interlocked motion of the links to lift one of the adjacent body parts connected to the first link or second link.

9. The robot according to claim 8,
    wherein the connector further comprises a gear part provided in the first link or second link, and configured to decelerate power from outside through the interlocked motion to increase an output torque.

10. The robot according to claim 9,
    wherein the gear part comprises a plurality of gears engaging adjacent gears, the gears arranged such that the farther away from the gear where power is applied, the greater the number or size of the teeth of the gears.

* * * * *